United States Patent
Duane et al.

[11] Patent Number: 6,106,487
[45] Date of Patent: Aug. 22, 2000

[54] EXCHANGE ACCESSORY FOR USE WITH A MONORAIL CATHETER

[75] Inventors: Patrick J Duane, Newcastle; Thomas K. Fitzmaurice, Oranswell; James Paul Gilson, Killrainey; Ronan Micheál Thornton, Corcullen, all of Ireland; David Leason, New York, N.Y.

[73] Assignee: AVE Connaught, Dublin-2, Ireland

[21] Appl. No.: 09/018,221

[22] Filed: Feb. 3, 1998

Related U.S. Application Data

[62] Division of application No. 08/363,514, Dec. 23, 1994, Pat. No. 5,836,306.

[51] Int. Cl.$^7$ .................................................... A61B 5/00
[52] U.S. Cl. .......................... 600/585; 604/95; 604/96; 604/280
[58] Field of Search .................... 600/585, 433, 600/434; 604/280, 281

[56] References Cited

U.S. PATENT DOCUMENTS

| | | | |
|---|---|---|---|
| 3,853,130 | 12/1974 | Sheridan | 600/433 |
| 5,176,651 | 1/1993 | Allgood et al. | |
| 5,318,535 | 6/1994 | Miraki | |
| 5,334,160 | 8/1994 | Ellis | 604/167 |
| 5,376,077 | 12/1994 | Gomringer | |
| 5,391,152 | 2/1995 | Patterson | |
| 5,407,432 | 4/1995 | Solar | |
| 5,413,560 | 5/1995 | Solar | |
| 5,423,331 | 6/1995 | Wysham | 600/585 |
| 5,460,185 | 10/1995 | Johnson et al. | |

Primary Examiner—Cary O'Connor
Assistant Examiner—Pamela Wingood
Attorney, Agent, or Firm—Sterne, Kessler, Goldstein & Fox P.L.L.C.

[57] ABSTRACT

An exchange accessory useful with monorail and other types of catheters has a hollow, elongated sleeve for insertion into a Tuohy-Borst connector or the like, and an enlarged head at its proximal end to restrain the sleeve from advancing with the catheter into the connector. The sleeve is slidably mounted on the catheter shaft so that it may be interposed between a sealing member within the connector and the catheter. The internal diameter of the sleeve is greater than and complementary with the external diameter of the catheter shaft to define a space about the catheter shaft sufficient to allow backbleed of blood therethrough in a controlled manner.

In one embodiment, the sleeve has a slotted head to accommodate a guidewire which may extend in parallel to the catheter shaft, for example, when used with a monorail type catheter. The slot permits the guidewire to extend proximal to the connector without bending or kinking. In another embodiment, the exchange accessory may be assembled onto a conventional catheter shaft. As a modification to these embodiments, an aperture may be provided for selectively engaging the catheter by closing the connector on the sleeve with the aperture aligned with a sealing member of the connector.

13 Claims, 3 Drawing Sheets

EXCHANGE ACCESSORY FOR USE WITH A MONORAIL CATHETER

This is a division of application Ser. No. 08/363,514, filed Dec. 23, 1994, now U.S. Pat. No. 5,836,306. Each of these prior applications is hereby incorporated herein by reference, in its entirety.

FIELD OF THE INVENTION

The present invention relates generally to a device for use with a catheter by medical personnel and, more particularly, to an exchange accessory for use with a "monorail" type catheter.

BACKGROUND OF THE INVENTION

Catheters may be introduced into the human body as part of diagnostic or treatment procedures. Such devices are typically introduced through arteries and are advanced to the site designated for diagnosis or treatment, which site may be a particular vessel or an organ, for example, the heart. In certain uses, a technique for advancing a diagnostic or treatment catheter and guidewire requires opening of a Tuohy-Borst connector, moving the catheter to the designated site within the body where diagnosis or treatment is to occur, and reclosing the connector, all of which steps are well known to skilled clinicians.

The aforementioned practice presents a number of difficulties. If the Tuohy-Borst connector is overtightened on reclosure, subsequent catheter movement and manipulation may be impaired. Also, closure is not reliable for the entire range of diameters of catheters which may be used, especially with respect to small diameter catheters, for example, those used in percutaneous transluminal coronary angioplasty ("PTCA") procedures, which make positive sealing closure of the Tuohy-Borst connector difficult. Further, known devices require the Tuohy-Borst connector to remain open while the catheter is manipulated which results in undesirable backbleed from the blood vessel when the catheter is introduced into the patient's vasculature through the connector. The backbleed may continue for an extended period of time while the catheter is being positioned, often causing complications in the PTCA procedure, and even conceivably, resulting in considerable loss of blood for the patient. The rate of backbleed is inversely related to the outside diameter of the catheter and relative to the fixed diameter connector so that as the catheter shaft diameter decreases, the rate of backbleed increases.

One known device for controlling backbleed while positioning an over-the-wire or fixed-wire catheter is described in U.S. Pat. No. 5,203,774 to Gilson et al., incorporated herein in its entirety. This device consists of a rigid sleeve assembled over the shaft of a catheter and shaped to fit into a Tuohy-Borst connector. The sleeve has an external diameter chosen so that when the connector is closed, a seal is formed between the sleeve and the connector, while still allowing for free movement of the catheter shaft in relation to the closed connector and for free movement of the guidewire housed within a lumen of the catheter. Backbleed is limited to the annulus between the inner diameter of the sleeve and the outer diameter of the catheter, diameters which are chosen to be complementary to minimize backbleed without compromising catheter movement. A disc-like flange or head is provided at the proximal end of the sleeve to limit axial motion of the sleeve within the connector.

On occasion, there is a need to exchange one catheter for another. For example, where only a very small balloon dilatation catheter can cross a stenosis, a pre-dilatation catheter may be used to partially dilate the stenosis so that a larger balloon dilatation catheter can be exchanged therefor and positioned across the stenosis to restore the vessel to a more natural, non-occluded diameter. It is difficult to perform a catheter exchange with an over-the-wire type catheter, the only type which may be used with the device disclosed in the '774 patent, because the operator must ensure that the guidewire remains in place across the stenosis while the shaft is being withdrawn. An extension guidewire, whose overall length is approximately the length of the balloon catheter, is attached to the proximal end of the guidewire prior to withdrawing the shaft so that the operator has a sufficient length wire to hold onto as the catheter is withdrawn and envelopes the proximal end of the guidewire. Guidewires with proximal ends that are suitably adapted to receive an extension guidewire are described in U.S. Pat. Nos. 4,917,103, 5,031,636 and 4,922,923 to Gambale et al.

The need for an extension wire and the difficulties associated with the exchange procedure using an over-the-wire type catheter are avoided when a "monorail" type catheter is used in lieu of the over-the-wire catheter design. The "monorail" catheter has the guidewire external to the shaft for most of the shaft's length. See U.S. Pat. No. 4,762,129 to Bonzel, the entire disclosure of which is incorporated herein, for an exemplary "monorail" type catheter. The guidewire is slidably received in an abbreviated or shortened lumen which extends only from the distal tip of the catheter to a more proximally located opening along the catheter shaft. This opening is sometimes referred to as an "exchange joint." This shortened lumen is typically between three and forty centimeters long. After a conventional length angioplasty guidewire has been advanced to the site of the stenosis, the monorail catheter can be threaded onto the externally extending proximal portion of the guidewire and introduced to the patient's vascular system through the Tuohy-Borst connector. The monorail catheter is then advanced through the guide catheter and beyond, alongside the guidewire with only its distal segment attached to and guided by the guidewire. The proximal portion of the catheter and the guidewire separately extend through the Tuohy-Borst connector in this procedure.

Previous to this invention, there was no device which would satisfactorily control backbleed out of a proximal connector or fitting yet also provide for a guidewire which extends proximally alongside a catheter, as in the monorail catheter design. Further, previous designs have required the operator to manually hold the guidewire in position during catheter manipulations and the like. There is a need for a device, heretofore unavailable, which provides backbleed control during and after placement of a monorail type catheter within a patient's vascular system, and which provides selective clamping of a guidewire for all varieties of catheters useful for diagnostic or treatment purposes.

SUMMARY OF THE INVENTION

According to one aspect of the invention, an exchange accessory which is useful with all varieties of catheters, including the monorail type catheter, is provided for performing diagnostic or treatment procedures in a controlled backbleed environment. The exchange accessory of the invention permits independent movement of the guidewire and catheter, or alternatively permits clamping of the guidewire while permitting movement of the catheter, for example, during an exchange procedure. The exchange accessory comprises a hollow, elongated sleeve which is adapted to be inserted between the shaft of a catheter and a sealable connector. The connector is conventionally attached to a guide catheter in a patient to provide access to the patient's vasculature. The sleeve is slidably mounted on the catheter shaft so that it may be interposed between a sealing member within the connector and the catheter while the catheter is being positioned within the patient. The sleeve portion has an internal diameter which is greater than and complementary with the external diameter of the shaft of the particular catheter so that the sleeve defines a space about the shaft of the catheter sufficient to allow backbleed of blood therethrough in a controlled manner. The material of which the sleeve is composed is chosen to be sufficiently rigid so as to not distort upon application of a compressive force by the connector. The sleeve has an enlarged head portion at its proximal end to restrain the sleeve from advancing with the catheter into the connector. According to the invention the exchange accessory may include an aperture for selectively and directly engaging a catheter shaft disposed within the sleeve by closing the connector on the sleeve with the aperture aligned with the sealing member of the connector.

According to another aspect of the invention, the exchange accessory may comprise two halves and be assembled onto or removed from a catheter shaft, at the operator's discretion. The exchange accessory according to this aspect of the invention includes longitudinally fixed securing means for securing the two halves of the sleeve around the catheter in slidable relation thereto.

According to a further aspect of the invention, the sleeve has a slot in the head portion to accommodate a guidewire which may extend in parallel to the catheter shaft, for example, when used with a monorail type catheter. The slot permits the guidewire to extend proximal to the connector without causing a bend or kink in the guidewire. Further, the exchange accessory according to this aspect of the invention may restrain the guidewire from axial motion when the connector is closed. Because the guidewire of a monorail type catheter resides external to the exchange accessory within the connector and along the exterior of the sleeve, closure of the connector causes the guidewire to be clamped in place between the connector's sealing member and the sleeve. Meanwhile, the catheter remains free to be advanced, withdrawn or positioned axially along the guidewire.

According to another embodiment of the invention, the exchange accessory may permit free motion of the guidewire when the connector is closed, even when the exchange accessory is used with a monorail-type catheter, by providing a lumen to house the guidewire, yet which minimally impacts control over backbleed.

These and other features and advantages of the invention will be readily apparent from the following detailed description of certain embodiments taken in conjunction with the accompanying unscaled drawings.

DETAILED DESCRIPTION OF THE INVENTION

Figure 1:
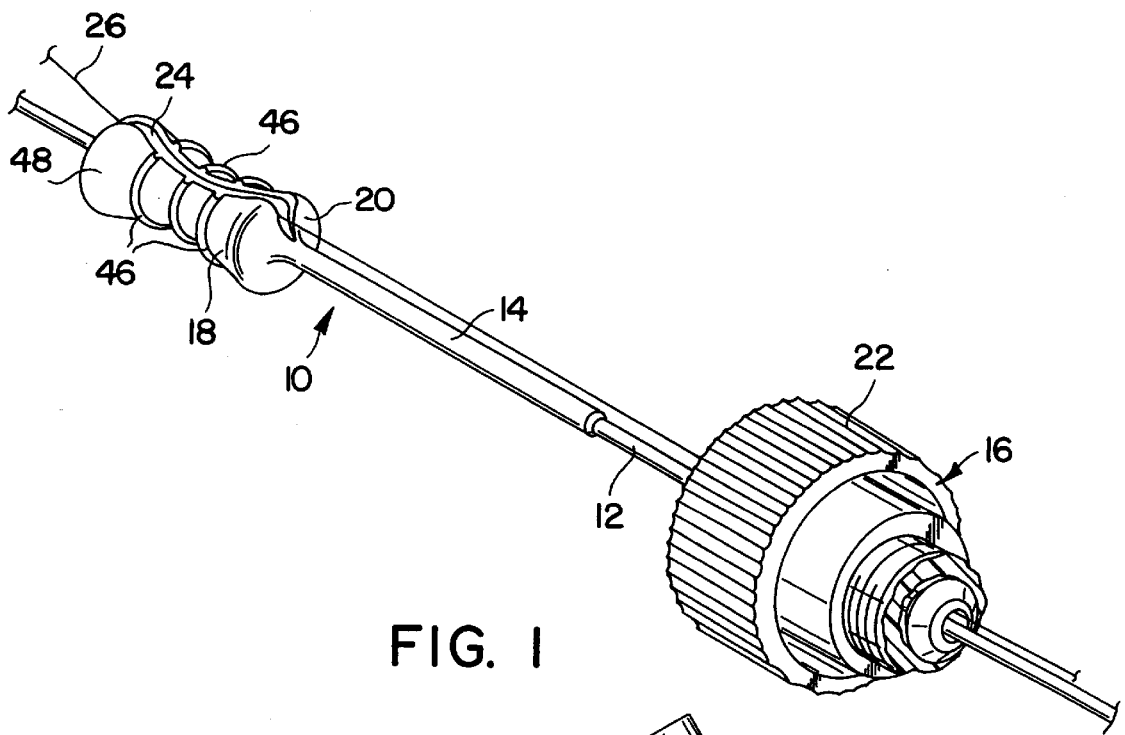
FIG. 1 is a perspective view of a presently preferred embodiment of the exchange accessory mounted on the shaft of a monorail catheter for insertion into a connector (shown broken away)

By way of overview and introduction, the exchange accessory of the present invention provides control over backbleed and clamps the guidewire. The exchange accessory permits independent movement of the guidewire and catheter, or alternatively permits clamping of the guidewire (by the Tuohy-Borst connector or a separate clip) while permitting movement of the catheter, for example, during an exchange procedure. The exchange accessory of the invention has utility with 2.7 French, 3.5 French, and other size catheters, with some constraints due to the limited space available for inserting the sleeve portion of the exchange accessory within the Tuohy-Borst connector. Likewise, the exchange accessory has utility with all varieties of catheters, including, for example, monorail and over-the-wire designs. In the following description, features common to one embodiment are given corresponding reference numerals in other Figures.

Referring now to FIG. 1, a preferred embodiment of the exchange accessory 10 is shown mounted on the proximal end of the shaft of a monorail catheter 12. The exchange accessory 10 includes a sleeve portion 14 that is adapted to be received in a connector 16 (shown broken away). The connector is conventionally mounted on the proximal end of a guide catheter (not shown), external to the patient. The connector 16 may be, for example, a Tuohy-Borst connector or any suitable connector which permits axial positioning of the catheter 12 and permits introduction of a contrast medium or medicament through the guide catheter and into the patient's vascular system. In accordance with one aspect of the invention, the sleeve portion 14 has an internal diameter which is greater than and complementary with the external diameter of the shaft of the particular catheter 12. Thus, the sleeve portion 14 defines a space about the shaft of the catheter 12 sufficient to allow backbleed of blood therethrough in a controlled manner. To facilitate discussion, the shaft of the catheter 12 is more generally referred to as the catheter 12.

The exchange accessory 10 further includes a head portion 18 which has an enlarged diameter relative to the sleeve portion 14. A shoulder 20 adjacent the sleeve portion 14 limits or restricts axial motion of the exchange accessory 10 within the connector 16 by abutting a rotatable end cap 22 located at and threadedly engaging the proximal end of the connector 16. Preferably, the head portion 18 is smaller in diameter than the end cap 22 to prevent inadvertent mutual rotation of the exchange accessory 10 with the end cap 22. Rotation of the exchange accessory 10 could cause a guidewire to "wrap" around the catheter 12. This would introduce undesirable drag against advancement and withdrawal of the catheter 12.

According to a presently preferred embodiment, the head portion 18 is provided with a slot 24 that is aligned coaxially with the sleeve portion 14. The slot 24 has a width sufficient to accommodate a guidewire 26, for example, an angioplasty guidewire which typically ranges from about 0.010 inch to 0.018 inch in diameter. The slot 24 preferably extends completely through the head portion 18 and substantially to the exterior surface of the sleeve portion 14.

Figure 2:
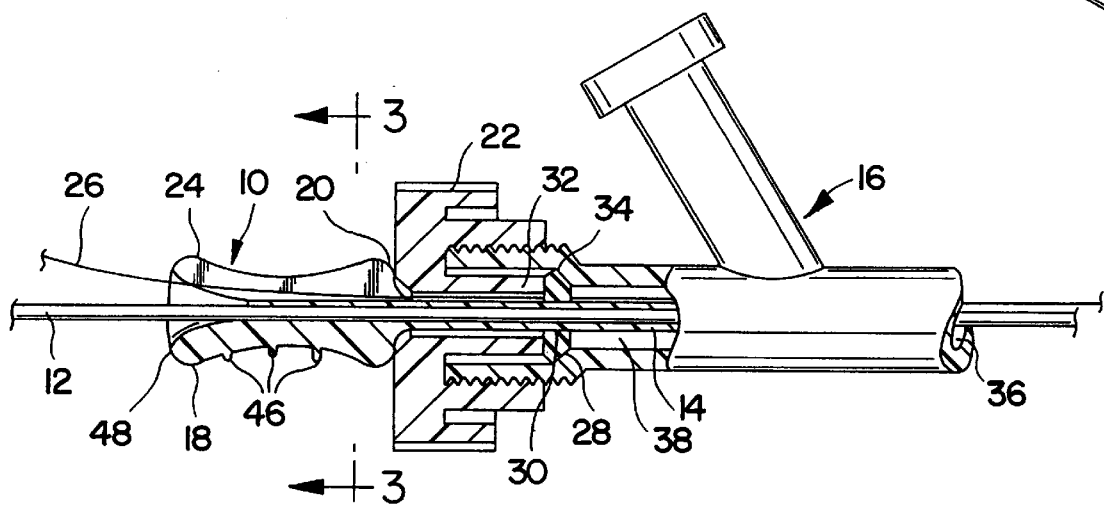
FIG. 2 is a side view partial cross-section of an exchange accessory engaged with a Tuohy-Borst connector.

FIG. 2 illustrates the exchange accessory 10 of the presently preferred embodiment in its intended environment. The exchange accessory 10 is shown fully inserted into connector 16 with the shoulder 20 of the exchange accessory 10 abutting the end cap 22 of the connector. The exchange accessory 10 extends into the connector 16 to a point distal to a sealing member 28 thereby isolating the catheter 12 from the sealing member 28. The connector 16 is of conventional, known design, such as the STRETCH™ Tuohy-Borst connector available from the USCI division of C.R. Bard, Inc., Billerica, Mass.

The connector 16 has an open position in which a bore 30 in sealing member 28 permits passage of fluid such as blood or objects such as the exchange accessory 10 or the guidewire 26 and a closed position in which the sealing member 28 substantially precludes passage of fluid or other objects. The connector 16 is opened and closed by compressing the sealing member 28 with a plunger 32 connected to the end cap 22. The end cap 22 and the connector 16 are threadedly joined in a manner such that rotation of the end cap 22 causes the plunger 32 to move toward or away from the sealing member 28.

More specifically, rotation of the end cap 22 causes the plunger to move toward the distal end of the connector 16 (to the right in FIG. 2). This causes the sealing member 28 to be compressed against a fixed shoulder portion 34 to constrict a lumen 36, which extends through the connector 16. As shown, the shoulder 34 tapers inwardly toward the distal end of connector 16. The sealing member 28 is conventionally made of an elastic material, such as silicone. The sealing member 28 is elastically resilient so that rotation of the end cap 22 in the opposite direction will cause the plunger to move toward the proximal end of the connector 16 and will permit the sealing member 28 to return to its unbiased state in which the bore 30 permits passage of fluids or other objects. The operator rotates the end cap 22.

With the exchange accessory 10 inserted fully into the connector 16, the sealing member 28 will seal against the sleeve portion 14, but not against the catheter 12. With the connector 16 thus closed, fluid flow through the lumen 36 is stemmed at the sealing member 28, with no fluid flowing in a region 38, external to the sleeve portion 14. Conversely, fluid flow through the sleeve portion 14 remains unchecked and is limited to an annulus or space 44 between the catheter 12 and the internal diameter of the sleeve portion 14 (see FIG. 3A).

While the catheter 12 is slidably disposed within the exchange accessory 10, the guidewire 26 resides external to the exchange accessory 10, within the slot 24 and along the exterior of the sleeve portion 14. Closure of the connector 16 by rotating end cap 22 causes the guidewire 26 to be clamped in place between the sealing member 28 and the sleeve portion 14. Thus, the guidewire 26 used with a monorail type catheter 12 is restrained from axial motion when the connector is closed about the exchange accessory 10 of the presently preferred embodiment. Although the connector 16 has clamped the guidewire 26 in place, for example, with the guidewire's distal region in place across a stenosis or at the site for treatment or diagnosis, the catheter 12 remains free to be advanced, withdrawn or positioned axially along the guidewire. The sleeve portion 14 must be sufficiently rigid to maintain the annulus 44 about the catheter 12 as the sealing member 28 presses against the exterior of the sleeve portion 14 when the connector 16 is closed; however, when the sleeve further includes guidewire lumens 100 and 108, described below in connection with FIGS. 6C–6F, slits 105,106 in the sleeve portion 14 permits the sealing member 28 to resiliently collapse the lumens 100,108 to a reduced diameter. Nevertheless, the annulus 44 about the catheter 12 must not distort when the connector 16 is closed.

At any time during the procedure a contrast or medicament may be introduced into the patient's vascular system through an opening 40 in side arm 42 of the connector 16.

Also seen in perspective in FIG. 1 and in cross-section in FIG. 2, are ribs 46 provided to facilitate handling of the exchange accessory 10. One or more ribs 46 may be provided between a proximal end 48 of the head portion 18 and the distal end (the shoulder 20). Ribs 46 may radially surround the head portion 18 (as shown) or be oriented coaxially with respect to the sleeve portion 14 (see element 46' in FIGS. 3B–D). Other like means for improving grippability of the exchange accessory may be employed in addition to, or instead of the ribs 46, such as knurling or checkering of the surface.

Figure 3A:
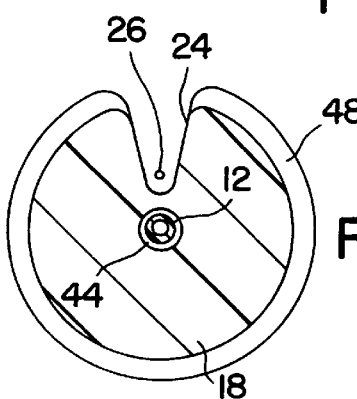
FIG. 3A is a cross-sectional view of the head of the exchange accessory according to the preferred embodiment taken along line 3—3 of FIG. 2, mounted on the monorail catheter.

FIG. 3A shows in cross-section the arrangement of the monorail type catheter 12 and the guidewire 26 within the exchange accessory 10 of the preferred embodiment. The exchange accessory is slidably mounted around the catheter 12 and defines an annular space 44 therebetween which extends through the head portion 18 and through the sleeve portion 14. The guidewire 26 is disposed in the slot 24 of the head portion 18 and extends generally parallel to the sleeve portion 14. The slot 24, being of sufficient width to accommodate the guidewire 26, permits the guidewire 26 to extend proximal to the connector 16 with the exchange accessory 10 fully inserted therein, without causing a bend or kink in the guidewire 26.

Figure 3C:
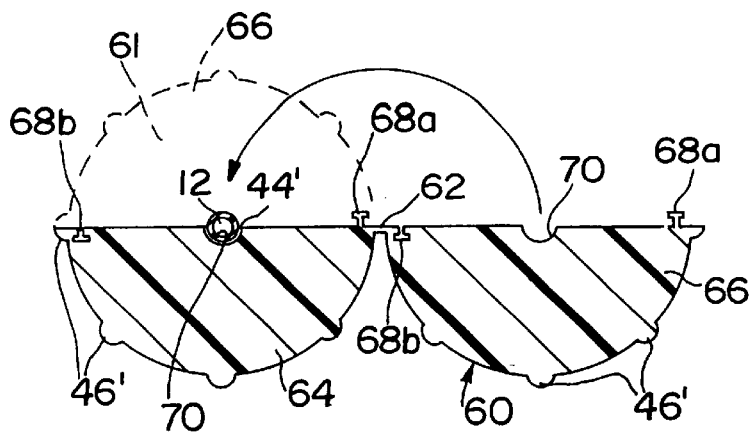
FIG. 3C is a cross-sectional view of a second embodiment of the exchange accessory head wherein the exchange accessory may be hingeably assembled to or disassembled from the catheter shaft.
Figure 3D:
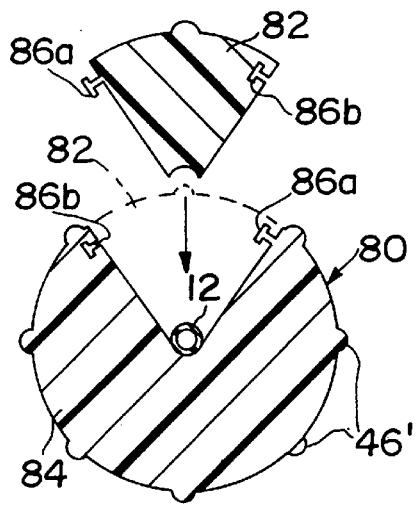
FIG. 3D is a cross-sectional view of a third embodiment of the exchange accessory head wherein the exchange accessory may be assembled to or disassembled from the catheter shaft by way of a removable segment.
Figure 3B:
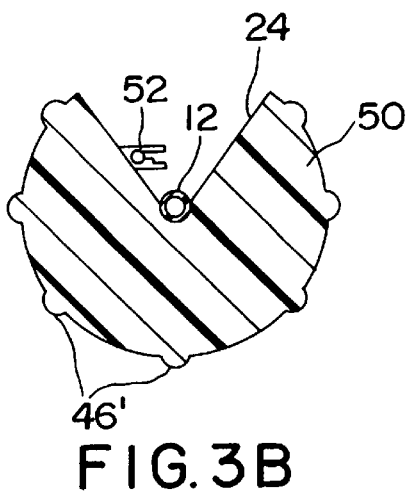
FIG. 3B is a cross-sectional view of a modification of the exchange accessory head showing a clip for restraining axial motion of a guidewire.
Figure 4:
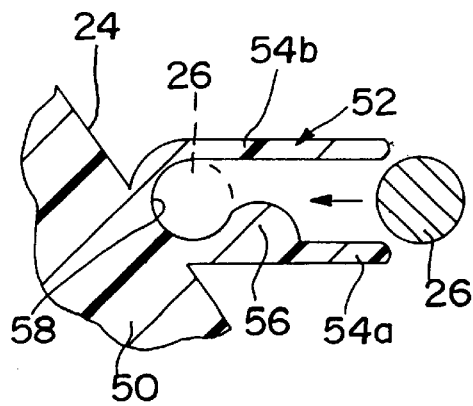
FIG. 4 is a detail view of the clip of FIG. 3B.

In FIG. 3B, a modified head portion 50 is shown in which a longitudinally fixed clip or clamping means 52 is positioned within the slot 24 for receiving the guidewire 26. As detailed in FIG. 4, the clip 52 includes flexible arms 54*a,b* which are spaced apart to freely receive the guidewire 26. The operator may urge the guidewire into a pocket 58 between arms 54*a,b* by snapping or gripping the guidewire beyond a resilient protuberance 56 on the inner surface and between the ends of at least one of the arms 54*a* (FIG. 4). The clip 52 substantially immobilizes or fixes the position of the guidewire 26 relative to the advancement of the catheter 12 through the patient's vasculature, regardless of whether the connector 16 is opened or closed. This enables the operator to concentrate on manipulating the catheter 12 without having to manually clamp the guidewire 26. Preferably, the clip 52 is integrally molded with the head portion 50.

The clip 52 while shown extending at a chord angle from a wall of the slot 24 may be oriented in other directions such as radially outward or radially inward. In any event, the principle of operation is the same but different orientations of the clip 52 with respect to the slot 24 may facilitate placement of the guidewire 26 therein. Further, while the clip 52 is shown positioned within the slot 24, the invention is not so limited. For example, the clip might be positioned along the perimeter of the head portion 18, adjacent the ribs 46.

FIG. 3C shows a second embodiment of an exchange accessory 60 according to the invention which has utility with fixed-wire, over-the-wire and monorail type catheters. This embodiment of the invention includes a hinge 62 along the head portion which permits the exchange accessory 60 to be assembled to or disassembled from the catheter 12. The head portion 61 comprises head sections 64,66 which rotate about the hinge 62 to cause complementary locking members 68a,b, which may be of any suitable shape or configuration, to engage each other. FIG. 3C illustrates two pairs of locking members 68a,b, although the invention is not so limited. Other means of securing the two halves of the sleeve together could be used with equal advantage. The catheter 12 is positioned within a semicircular bore 70 provided in each of the head sections 64,66 so that when the sections are rotated to engage locking members 68a,b (head section 66 shown in phantom), the catheter 12 is slidably housed within the head portion 61 with an annular space 44' therearound (see FIG. 6B). The catheter 12 is also slidably housed within a pair of sleeve sections 74,76 which form two halves of the sleeve, in the direction of elongation. Each of the sleeve sections 74,76 is preferably hemispherical in cross-section so that when the sleeve sections 74,76 engage each other, as when the head portion 61 is assembled, a cylindrical sleeve 77 results. Each of the sleeve sections 74,76 is attached to or integrally formed with a respective one of the head sections 64,66 (see FIG. 6B). Preferably, one of the sleeve sections 74,76 and the head sections 64,66 is formed with complementary tongued and grooved edges 72a,b to enhance the strength of the sleeve 77 and resist distortion of the annulus 44' when inserted into the connector 16 and compressed by the sealing member 28.

Figure 6A:
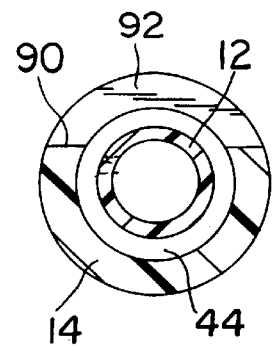
FIG. 6A is a cross-sectional view taken along line 6—6 of FIG. 5.
Figure 6B:
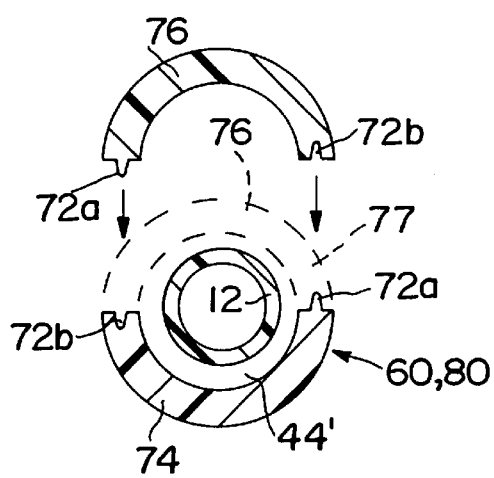
FIG. 6B shows the sleeve portion of the exchange accessory of either of the embodiments shown in FIGS. 3C or 3D.

FIG. 3D shows a third embodiment of an exchange accessory 80 which may be assembled to or disassembled from the catheter 12 in a different manner than in the embodiment of FIG. 3C. This embodiment 80 includes a removable segment 82 which may be slid or snapped into a head portion 84. Complementary resilient lock and key portions 86a,b hold the removable segment 82 in place. The removable segment 82 is attached to or integrally formed with one of the sleeve sections 74,76 (FIG. 6B). The assembled exchange accessory 80 defines the space 44' surrounding the shaft of the catheter 12, as in the embodiment of FIG. 3C.

Figure 5:
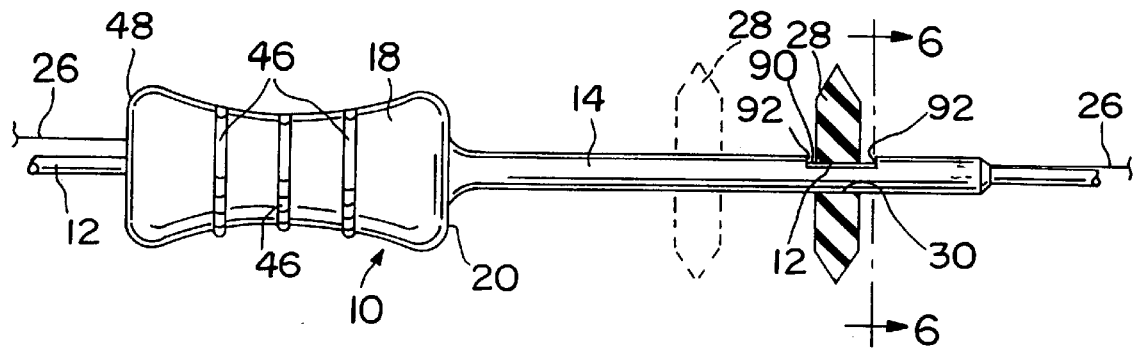
FIG. 5 shows a modification of the exchange accessory wherein the sleeve includes an aperture for selectively gripping the catheter.

A further modification of any of the foregoing embodiments is shown in FIG. 5. In FIG. 5, the sleeve portion 14 is provided with an aperture 90 through the sleeve portion 14 to expose the catheter 12 disposed therein, as seen in FIG. 6A. The aperture 90 permits the operator to selectively clamp or grippingly engage the catheter 12 within the connector 16 by axially positioning the exchange accessory within the connector 16. For ease of illustration, only the sealing member 28 of the connector 16 is shown in FIG. 5. When the exchange accessory is fully inserted into the connector, that is, with the shoulder 20 abutting the end cap 22, the sealing member 28 is positioned along the sleeve portion 14 at the location shown in phantom. In this fully inserted position, closure of the connector will cause the sealing member 28 to clamp down around the sleeve portion 14 (or 77), but not the catheter 12. The catheter 12 remains free to be axially positioned at the operator's discretion. The operator may hold the catheter in place, for example, in an attempt to prevent proximal backtrack of the catheter as a dilatation balloon is inflated against a resistively rigid stenosis, by sufficiently withdrawing the exchange accessory to align the sealing member 28 with the aperture 90 (as shown). Once so aligned, the sealing member occupies the aperture and will resist further withdrawal of the sleeve, unless the connector is opened further so that the bore 30 of the sealing member 28 restores to a diameter sufficient to clear a surface 92 at the distal end of the aperture (see FIG. 6A). With the sealing member 28 aligned with the aperture 90, the connector may be closed to clamp the sealing member 28 against the catheter 12.

Figure 6C:
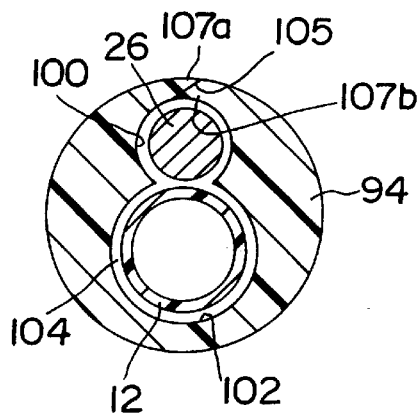
FIGS. 6C–6F show four different cross-sectional views of the exchange accessory in which the sleeve is provided with a lumen for the guidewire in addition to the catheter lumen.
Figure 6E:
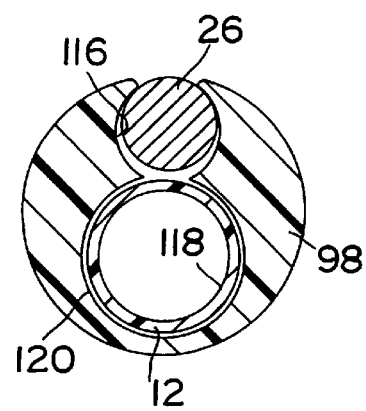
Figure 6D:
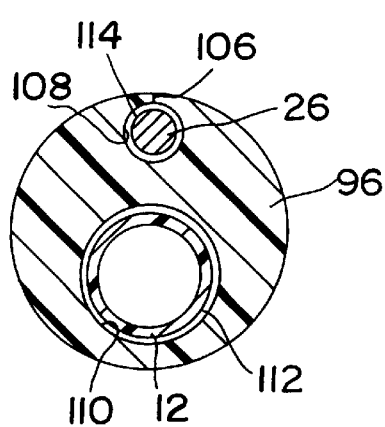

FIGS. 6C–6F illustrate alternative embodiments of the exchange accessory according to another aspect of the invention. These embodiments include sleeve portions 94,96,98,99 which have been particularly modified to accommodate the separately, proximally extending guidewire 26 used with a monorail type catheter 12. In each of these embodiments, the guidewire 26 resides within the sleeve portion along with the shaft of the catheter 12. In FIG. 6C, the guidewire 26 and the catheter 12 extend axially in lumens 100, 102 which communicate with one another. A space 104 between the guidewire 26 and the catheter 12 within lumens 100,102 allows for controlled backbleed when the connector 16 is closed around the sleeve 94. Optionally, a slit 105 may extend from the guidewire lumen 100 to the exterior of the sleeve to permit the guidewire 26 to be "peeled" away from the exchange accessory. As shown in FIG. 6C, the slit 105 is tangentially directed through the sleeve to form a pair of overlapping members or ends 107a,b, however the invention is not so limited. In FIG. 6D, for example, a slit 106 is radially oriented. Despite the presence of slits 105,106 guidewire lumens 100,108 are enclosed insofar as they separate or isolate the guidewire from the sealing member 28 of the connector 16. Further, when the connector 16 is closed by compressing the sealing member 28 about the sleeve 94, overlapping members 107a,b move relative to one another so as to constrict the guidewire lumen 100 for so long as the sealing member exerts a force against the sleeve 94. Preferably, the guidewire lumen 100 resiliently restores to the diameter shown in FIG. 6C so that the guidewire can be axially moved when the connector is subsequently opened.

In FIG. 6D, the sleeve 96 has the guidewire and catheter lumens 108,110 separately extending in an axial direction. A space 112 between the catheter 12 and the lumen 110 and a space 114 between the guidewire 26 and the lumen 108 allow for controlled backbleed when the connector 16 is closed around the sleeve 96. As noted above, the slit 106 is radially oriented through the sleeve and permits the guidewire 26 to be peeled therefrom while isolating the guidewire from the sealing member 28 when the sleeve is inserted into the connector 16.

In FIG. 6E, a guidewire lumen 116 is provided in the sleeve 98 which is smaller in circular diameter than the guidewire 26. When the connector 16 is closed around the sleeve 98 by compressing the sealing member 28, the guidewire lumen 116 collapses upon the guidewire 26. The collapsed lumen 116 grasps the guidewire 26 and restrains the guidewire from axial motion. In addition, the sealing member 28 is compressed into contact with the guidewire 26 as a separate mechanism to restrain axial motion of the guidewire 26. Meanwhile, the guidewire 26 maintains the internal diameter of a lumen 118 around the catheter 12 greater than and complementary with the external diameter of the catheter 12. As a result, a space 120 is defined between the catheter 12 and the sleeve 98 sufficient to allow backbleed of blood therethrough in a controlled manner while permitting free axial motion of the catheter 12.

Figure 6F:
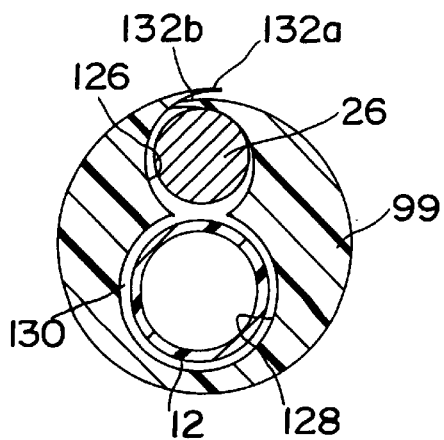

FIG. 6F shows a modification of the embodiment of FIG. 6E. There, a sleeve 99 has a guidewire lumen 126 which is again smaller in diameter than the guidewire 26. Unlike the embodiment of FIG. 6E, the sealing member 28 is isolated from contact with the guidewire 26 by means of overlapping members 132a,b, even when there is no radially compressive force being applied by the sealing member 28 of the connector 16, as shown in FIG. 6F. When the connector 16 is closed around the sleeve 99 by compressing the sealing member 28, the guidewire lumen 126 collapses upon the guidewire 26, and the overlapping members 132a,b move relative to one another so as to constrict the guidewire lumen 126 for so long as the sealing member exerts a force against the sleeve 99. The collapsed lumen 126 grasps the guidewire 26 and restrains the guidewire from axial motion. Meanwhile, the guidewire 26 maintains the internal diameter of a lumen 128 around the catheter 12 greater than and complementary with the external diameter of the catheter 12. As a result, a space 130 is defined between the catheter 12 and the sleeve 99 sufficient to allow backbleed of blood therethrough in a controlled manner while permitting free axial motion of the catheter 12. Preferably, the guidewire lumen 126 resiliently restores to the diameter shown in FIG. 6F so that the guidewire can be axially moved when the connector is subsequently opened.

Experiments have confirmed a reduction in backbleed rate when a sleeve is inserted between a catheter shaft and an open Tuohy-Borst connector. See U.S. Pat. No. 5,203,774 to Gilson et al.

The exchange accessory may be composed of any suitable material such as a metal or plastic, and is preferably composed of a thermoplastic material, and more preferably acetal. Regardless of the material chosen, at least the sleeve portion of the exchange accessory must be sufficiently rigid to prevent the sealing ring or member of the Tuohy-Borst connector or the like from distorting the catheter receiving lumen of the sleeve. The head and sleeve portions may be of unitary construction, and, in the case of the embodiment of FIG. 3C, the hinge 62 may comprise a thin layer of material which bridges head sections 64,66 such as a "living hinge" or the like, which may be integrally formed with the head sections 64,66. The exchange accessory may be made by standard manufacturing techniques, for example, injection molding, machining or casting. The inner surfaces should have low frictional characteristics to allow for ease of movement of the catheter within it. The exchange accessory may, if desired, be coated with a low friction, hydrophobic material such as PTFE or a hydrophilic material.

The procedure for using the exchange accessory with a monorail type catheter is as follows. Before the procedure is to begin, vascular access is established in a conventional manner with a guide catheter and the Tuohy-Borst connector 16. Depending upon the particular procedure, the guide catheter is typically introduced, using an introducer/dilator, through either the groin, wrist, or below the elbow. The guidewire 26 is then advanced through the connector 16 to the designated site for treatment or diagnosis, for example, a coronary artery. Once the guidewire 26 has been positioned as desired, the connector 16 is closed around the guidewire 26 to stem backbleed and hold the guidewire 26 in place while the catheter 12 is prepared for insertion into the patient.

If the catheter 12 does not already have an exchange accessory assembled on its shaft, then the exchange accessory 60 or 80 may at this time be assembled onto the catheter shaft 12, with the sleeve portion 77 facing the distal end of the catheter 12.

Next, the catheter 12 is backloaded onto the guidewire's 26 proximal end, the connector 16 is opened, and the catheter is advanced until the exchange joint (of the monorail catheter) has passed the sealing member 28 of the connector 16. The exchange accessory is then slid along the catheter shaft into the connector so that it is interposed between the sealing member 28 and the catheter 12. The connector 12 is then tightened about the sleeve portion 14 to secure the exchange accessory in position. At this point in the procedure, with the catheter 12 not yet having been advanced to the designated site, backbleed has been controlled by limiting fluid flow to the annulus defined between the inner diameter of the sleeve and the outer diameter of the catheter, which have been advantageously chosen to be complementary. With the exchange accessory of the preferred embodiment, the guidewire is clamped by the connector 16 to hold it in position while the catheter is advanced through the patient's vasculature. This frees the operator's hands for manipulating the catheter 12. The procedure is then completed, in conventional manner.

To exchange one catheter 12 for another, the catheter is withdrawn until its exchange joint reaches the exchange accessory. This position is conventionally determined by an exit marker on the catheter shaft, proximal to the exchange joint. The connector 16 is then opened to release the guidewire 26 and then the exchange accessory and catheter are withdrawn from the guidewire 26. The new catheter may then be introduced in the same manner as the catheter that has just been withdrawn.

The present invention may be used with several types of catheters including monorail and over-the-wire catheter designs. For example, with an over-the-wire catheter design, the operator would proceed generally as above. Moreover, although the invention has been described in detail with particular reference to particular embodiments thereof, it should be understood that the invention is capable of other and different embodiments, and its details are capable of modifications in various obvious respects. As would be readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

We claim:

1. An exchange accessory comprising:

a hollow, elongated sleeve having an enlarged head and being separated into two halves in the direction of elongation; and longitudinally fixed securing means for securing the two halves of the sleeve around a catheter in slidable relation thereto.

2. An exchange accessory as claimed in claim 1, wherein the enlarged head has a slot sized to accommodate a guidewire.

3. An exchange accessory adapted for use with a catheter and for insertion into a connector of the type including a sealing member to close the connector when compressed by application of an external force by an operator, comprising:

a hollow, elongated sleeve adapted to be received within the connector and to slidingly receive the catheter, the sleeve having an enlarged head portion at a proximal portion of the sleeve to restrain the sleeve from advancing with the catheter into the connector, the sleeve being separated into two halves in the direction of elongation; and longitudinally fixed means for securing the two halves of the sleeve around the catheter in slidable relation thereto.

4. An exchange accessory as claimed in claim 3, wherein the enlarged head has a slot sized to accommodate a guidewire.

5. An exchange accessory as claimed in claim 3, wherein the two halves of the sleeve are hingeably connected by a bridge.

6. An exchange accessory as claimed in claim 5, wherein the bridge is integrally formed with the two halves.

7. An exchange accessory as claimed in claim 3, wherein the securing means comprise complementary tongue and groove formations on at least one of the sleeve and head.

8. An exchange accessory as claimed in claim 3, wherein the sleeve and the catheter define a space therebetween, the sleeve being sufficiently rigid to maintain the space when received and sealed within the connector.

9. An exchange accessory as claimed in claim 3, wherein the enlarged head restricts axial motion of the sleeve within the connector.

10. An exchange accessory as claimed in claim 3, wherein the head includes a means for selectively clipping a guidewire to the exchange accessory to fix the position of the guidewire relative to the exchange accessory while the catheter remains slidable thereto.

11. An exchange accessory as claimed in claim 1, wherein the two halves of the sleeve are hingeably connected by a bridge.

12. An exchange accessory as claimed in claim 11, wherein the bridge is integrally formed with the two halves.

13. An exchange accessory as claimed in claim 1, wherein the securing means comprise complementary tongue and groove formations on at least one of the sleeve and head.

* * * * *

UNITED STATES PATENT AND TRADEMARK OFFICE
CERTIFICATE OF CORRECTION

PATENT NO. : 6,106,487
DATED : August 22, 2000
INVENTOR(S) : Duane et al.

It is certified that error appears in the above-identified patent and that said Letters Patent is hereby corrected as shown below:

<u>Column 10, claim 1,</u>
Line 52, after "head" insert -- at a proximal portion thereof --.

Signed and Sealed this

Second Day of April, 2002

Attest:

JAMES E. ROGAN
*Attesting Officer*       *Director of the United States Patent and Trademark Office*